United States Patent [19]
Salo et al.

[11] Patent Number: 5,584,868
[45] Date of Patent: *Dec. 17, 1996

[54] CARDIAC STIMULATING APPARATUS AND METHOD FOR HEART FAILURE THERAPY

[75] Inventors: Rodney W. Salo, Fridley; Julio C. Spinelli, Shoreview; Bruce A. Tockman, Minneapolis, all of Minn.

[73] Assignee: Cardiac Pacemakers, Inc., St. Paul, Minn.

[ * ] Notice: The term of this patent shall not extend beyond the expiration date of Pat. No. 5,334,222.

[21] Appl. No.: 281,476

[22] Filed: Jul. 27, 1994

Related U.S. Application Data

[63] Continuation of Ser. No. 970,893, Nov. 3, 1992, Pat. No. 5,334,222.
[51] Int. Cl.$^6$ ..................................................... A61N 1/39
[52] U.S. Cl. ................................................................. 607/17
[58] Field of Search ................................. 607/24, 17, 14, 607/18

[56] References Cited

U.S. PATENT DOCUMENTS

| 4,730,619 | 3/1988 | Koning et al. | 607/17 |
| 4,928,688 | 5/1990 | Mower . | |
| 5,024,222 | 6/1991 | Thacker . | |
| 5,226,414 | 7/1993 | Vandegriff et al. | 607/17 |

OTHER PUBLICATIONS

"Hemodynamic Effect of Physiological Dual Chamber Pacing in a Patient with End–Stage Dilated Cardiomyopathy: A Case Report" By Hajime Kataoka, Pace, vol. 14, Sep. 1991, pp. 1330–1335.

"Usefulness of Physiologic Dual–Chamber Pacing in Drug–Resistant Idiopathic Diluted Cardiomyopathy" by Hochleitner, et al, The American Journal of Cardiology, vol. 66, pp. 198–202.

Primary Examiner—William E. Kamm
Assistant Examiner—Scott M. Getzow
Attorney, Agent, or Firm—Haugen and Nikolai, P.A.

[57] ABSTRACT

A cardiac rhythm management device and method includes a dual-chamber pacemaker especially designed for treating congestive heart failure and a defibrillator as a back-up measure. The device incorporates a programmed microcontroller which is operative to adjust the AV delay of the pacemaker to a minimum or maximum length consistent with optimal cardiac function. The cardiac stimulator includes apparatus for sensing cardiac function from cycle-to-cycle and determining whether incremental changes made to the AV delay interval enhances or worsens the measured cardiac function. On each iterative cycle, the AV delay interval is changed, either incremented or decremented, until a cross-over point is reached in which it is noted that the cardiac function ceases to improve and this is followed with a further incremental adjustment in an opposite direction to compensate for any overshoot. By providing a cardiac defibrillator in combination with the pacing device with closed-loop control of the AV interval, incidences of sudden death due to lethal arrhythmias is reduced.

5 Claims, 4 Drawing Sheets

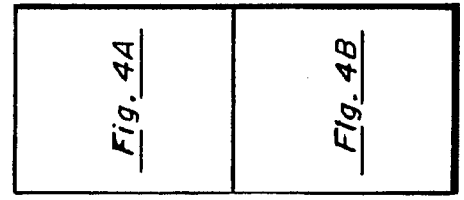
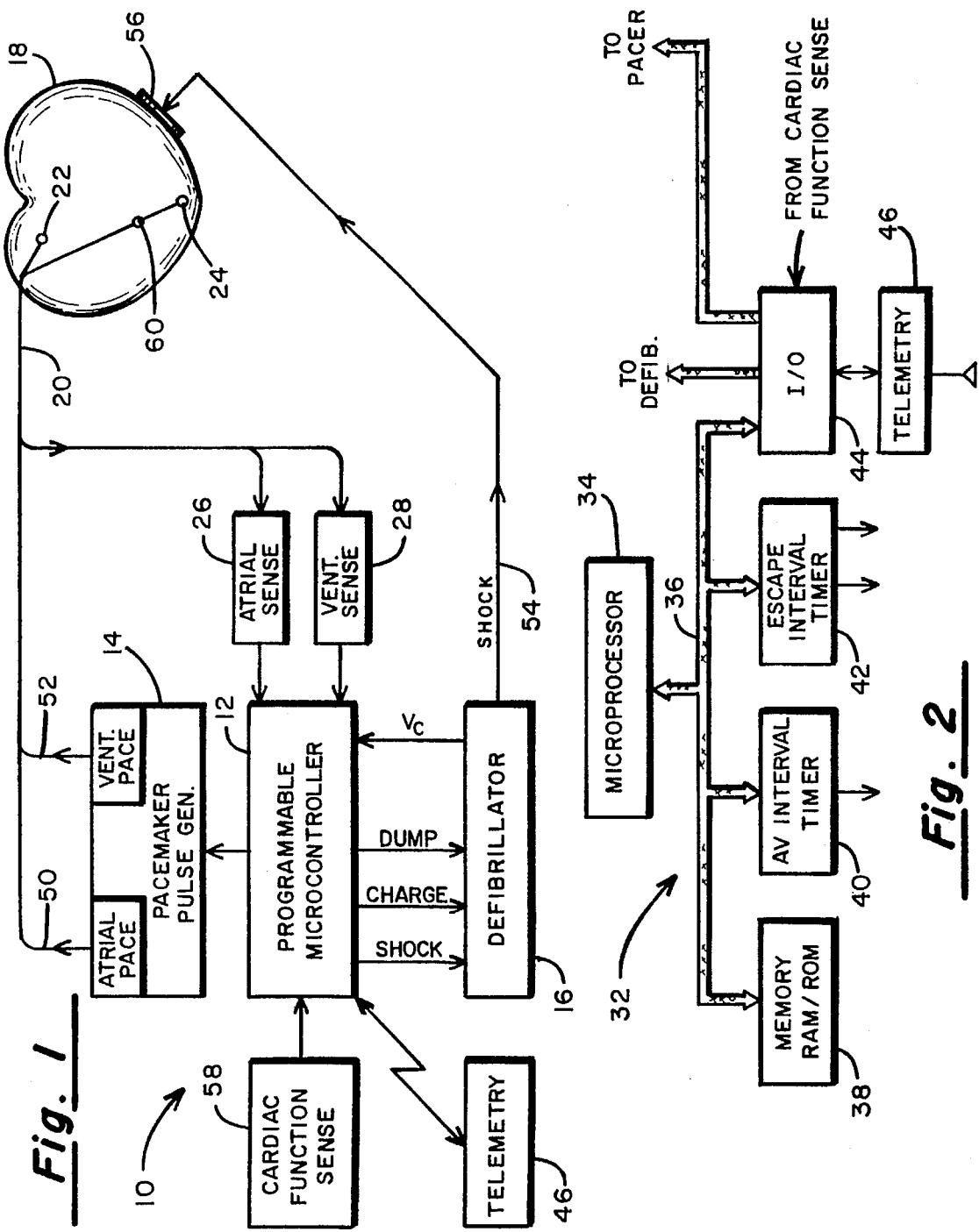

5,584,868

CARDIAC STIMULATING APPARATUS AND METHOD FOR HEART FAILURE THERAPY

CROSS-REFERENCE TO RELATED APPLICATION

This is a continuation of application Ser. No. 07/970,893, filed on Nov. 3, 1992 now U.S. Pat. No. 5,334,222.

BACKGROUND OF THE INVENTION

I. Field of the Invention

This invention relates generally to an implantable cardiac rhythm management apparatus, and more particularly to an improved device and method of operating the device to make it efficacious in the treatment of congestive heart failure.

II. Discussion of the Prior Art

Congestive heart failure (CHF) is an insidious disease affecting at least two million Americans. Patients diagnosed with heart failure have such a poor long-term prognosis (the average life span is five years) that it is tantamount to a death sentence. Thus, the potential market for successful therapy is not only large but highly motivated.

In the past, implantable cardiac pacemakers have principally been used to treat heart rate disorders, including bradycardia and tachycardia. Marguerite Hochleitner and her co-workers in the Department of Medicine of the University of Innsbruck published a paper called "Usefulness of Physiologic Dual-Chamber Pacing in Drug-Resistant Idiopathic Dilated Cardiomyopathy" in the *American Journal of Cardiology* (Vol. 66, Jul. 15, 1990, pp. 198–202) describing a study on a series of patients as to the beneficial effects of physiologic, dual-chamber (DDD) pacing in the treatment of end-stage idiopathic dilated cardiomyopathy. The pacemakers were implanted with the atrial electrode positioned near the right auricle and the ventricular electrode in the apical region of the right ventricle. Externally microprogrammable pacemakers, allowing reprogramming of the atrioventricular (AV) interval, were used. The AV interval was set at 100 milliseconds, this value being chosen as the shortest possible AV delay which would not significantly impair cardiac function. A marked improvement in cardiac function in most of the patients in the study resulted. For example, a remarkable improvement was noted in left ventricular ejection fraction, a reduction in heart size, a decrease in heart rate with tachycardia patients and an increase in heart rate for patients with bradycardia.

The devices described in the Hochleitner paper are not capable of adjusting the AV interval to fit the patient's changing condition after implant. While they do allow a change in AV interval through external reprogramming by the physician, optimization of AV interval through closed loop control is not involved. Moreover, those devices did not include a means for converting a fibrillating heart to sinus rhythm.

Current dual chamber pacemakers that allow for self-adjustment of the AV interval use an algorithm based entirely on rate. This shortening of AV interval with increased rate is merely designed to mimic the shortening of the PR interval which occurs in normal individuals with increases in rate. Patients in heart failure, however, will require adjustments in AV interval which are independent of rate and are, instead, a function of the patient's condition, posture, etc. Moreover, the AV shortening required with rate increases in these patients may not be identical to that for normal individuals.

In a paper entitled "Hemodynamic Effect of Physiological Dual Chamber Pacing in a Patient with End-Stage Dilated Cardiopathy: A Case Report" by Kataoka (Pace, Vol. 14, September 1991, pp. 1330–1335) describes the treatment of a patient in CHF using a DDD pacemaker. Again, the pacemaker described in this paper, while adjustable via an external transcutaneous programmer, did not provide for self-adjustment to meet changing conditions of the patient. Kataoka recommended that invasive hemodynamic measurements and a Doppler flow study be carried out to define an optimal AV interval but, as mentioned, the system described therein is basically open-loop with no feedback being provided for automatically adjusting AV interval to a value that optimizes systolic and diastolic function. None of the reported devices incorporate arrythmia detection and/or defibrillation backup.

SUMMARY OF THE INVENTION

The novelty of the device and method of the present invention centers around the ability to monitor physiological parameters associated with ventricular ejection and filling and to use this information in a closed-loop system to modify the sequence of pacing impulses to one or more chambers of the heart in order to optimize the performance of the heart and in having the ability to rescue the patient with a high energy shock if a malignant ventricular arrythmia develops. In implementing the system and method, a number of parameters, indicative of cardiac function, are monitored to determine whether the applied pacing sequence is optimal. However, the exact parameter is not as important as the overall strategy which is to (1) insure that sufficient time is available for the ventricles to fill with blood; and (2) to guarantee that this increased blood volume has not compromised the systolic (ejection) function of the heart. (Increased preload, i.e., ventricular filling, may result in decreased cardiac output in the severely compromised heart.)

In a conventional, prior art dual chamber pacemaker there is generally provided circuitry for sensing atrial and ventricular depolarization events, whether paced or natural, and circuitry for appropriately stimulating cardiac tissue. A programmable microcontroller is also contained within the implanted module and it is capable of receiving as inputs the signals from the atrial and ventricular sensing circuits so that stimulating pulses, when necessary, will be applied to the heart at the conclusion of a predetermined AV interval following the detection of an atrial event. The pacemaker of the present invention, in addition, includes an appropriate sensor whereby the electromechanical interval (EMI) of the heart can be measured. EMI is equal to the AV delay plus the pre-ejection period (PEP), the ejection time (ET) and the mean early filling time (MEFT). Suitable sensors may include, for example, an accelerometer to monitor heart sounds and an intracardiac impedance sensor for measuring the time variation in intracardiac impedance due to the influx and outflow of blood therefrom. With this information, along with knowledge of the atrial (or ventricular) cycle length (ACL), it is possible to determine an initial estimate of the AV interval using the formula:

$$AV_{est} = ACL - (PEP + ET + MEFT)$$

This $AV_{est}$ value becomes an initial estimate for establishing the AV interval for the implanted dual chamber pacemaker.

To further optimize this value, it is necessary to utilize a sensor which is sensitive to cardiac function, either systolic function or diastolic function. Here, heart sounds, sinus rate, perfusion, RV end-systolic pressure, peak rate of change of pressure with respect to time, right ventricular stroke volume or peak rate of change of volume with respect to time and peak aortic or pulmonic flow are available alternatives for assessing systolic function. Diastolic function can be monitored with an implantable doppler flow device measuring tricuspid or mitral flow. One potential measure of diastolic function is the ratio of peak flow during fast-filling, E, and during atrial contraction, A. The ratio E/A is a valid indicator of diastolic function since an increase in E/A is generally considered to indicate an improvement in diastolic function.

In accordance with the algorithm embedded in the programmable microcontroller, the AV interval may be changed from the $AV_{est}$ value, as computed above, in increments to a predetermined limit while simultaneously monitoring cardiac function. The AV interval in a narrow range around $AV_{est}$ with maximal cardiac function is then employed for subsequent pacing. The frequency at which the AV interval is updated as well as the maximum size of the AV interval increment, the maximum allowable AV interval, and the threshold at which cardiac function change is considered significant comprise programmable parameters for the pacemaker.

The device and associated pacing leads may be arranged to stimulate the right ventricle, the left ventricle or both the left and right ventricles simultaneously or separately.

In addition to providing automatic AV delay adjustment to optimize cardiac function in patients suffering from congestive heart failure, the device of the present invention also incorporates means for detecting arrhythmias, such as ventricular tachycardia, ventricular fibrillation and a means for delivering a cardioverting shock in an attempt to restore sinus rhythm. This capability is desirable in an implantable device for treating CHF in that those patients exhibit a high incidence of potentially lethal arrhythmias.

The foregoing features, objects and advantages of the invention will become apparent to those skilled in the art from the following detailed description of the preferred embodiment, especially when considered in conjunction with the accompanying drawings.

DESCRIPTION OF THE DRAWINGS

FIG. 1 is a block diagram of the preferred embodiment of the invention;

FIG. 2 is a block diagram of a microprocessor-based programmable microcontroller;

DESCRIPTION OF THE PREFERRED EMBODIMENT

Figure 3:
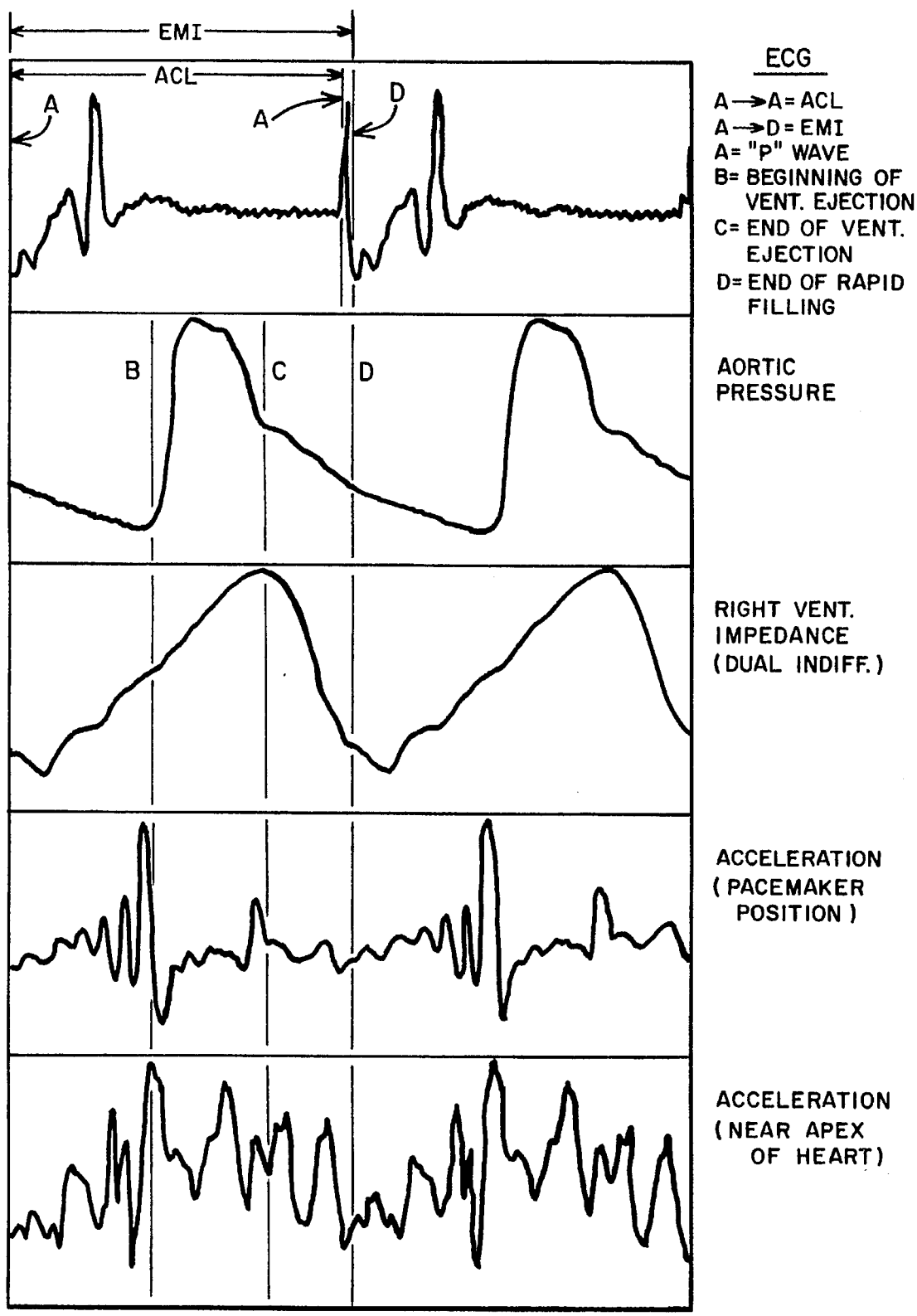
FIG. 3 is a diagram comparing a typical ECG waveform in time coincidence with the corresponding heart sounds and illustrating the manner in which aortic pressure, ventricular pressure and ventricular volume vary over the cardiac cycle.

Referring first to FIG. 1, there is illustrated a block diagram of an implantable cardiac rhythm management device embodying the present invention. It is indicated generally by numeral 10 and the intelligence for controlling the system is resident in a programmable microcontroller 12 which oversees the operation of both a bradycardia pacemaker 14 and a back-up defibrillator 16. The pacemaker portion of the system 14 is connected to the heart 18 by means of an endocardial lead 20 having first electrodes 22 for sensing atrial activity and second electrodes 24 for sensing and pacing one or both ventricles. The atrial sensing lead 22 is coupled through a conductor in the lead 20 to an atrial sense amplifier/filter circuit 26 whose output is fed to the programmable microcontroller 12. Likewise, the ventricular sense electrode is coupled through a conductor in the lead 20 to a ventricular sense amplifier/filter 28 and its output is also fed to the programmable microcontroller.

Those skilled in the art will appreciate that if a unipolar lead arrangement is employed, only a single electrode 24 need be incorporated on the lead 20, the metal can of the pacemaker serving as the return or indifferent electrode. In the case of a bipolar arrangement, two relatively closely spaced electrodes are positioned within the right ventricular chamber of the heart.

The programmable microcontroller 12 is identified generally by numeral 32 in FIG. 2 and comprises a microprocessor 34 having an internal bus 36 allowing bidirectional communication with a memory 38, an atrial ventricular interval timer 40, an escape interval timer 42 and an input/output (I/O) circuit 44. A telemetry circuit 46 is coupled to one I/O port and permits a two-way communication between the implanted rhythm management device 10 and an external programmer (not shown).

The microprocessor 34, working through the escape interval timer 42, provides control signals to the pacemaker pulse generator 14 for delivering either atrial stimulating pulses over the conductor 50 to the electrode 22 positioned in the right atrium or ventricular pacing pulses over the conductor 52 leading to one or more ventricular stimulating electrodes 24. In this manner, the cardiac rhythm management device of the present invention has the capability of providing biventricular pacing in accordance with the teachings of the Mower U.S. Pat. No. 4,928,688, which is assigned to the assignee of the present invention.

In addition to controlling the pacemaker pulse generator 14, the programmable microcontroller 12 also is connected in controlling relating to an implantable defibrillator circuit 16 capable of providing a high energy shock over lead 54 to an appropriate electrode 56, here shown as an epicardial patch. In particular, the programmable microcontroller 12 is responsive to the frequency and the rate of onset of ventricular depolarization signals picked up by the ventricular sense amplifier/filter 28 and, in accordance with a prescribed algorithm, determines whether ventricular fibrillation is occurring. If so, the microcontroller sends a signal to the defibrillator 16 to cause charging of its high voltage storage capacitors and then will deliver either a shock command or a dump command to the defibrillator, depending upon whether the defibrillation episode is still persisting at the time that the defibrillator 16 returns a signal to the programmable microcontroller 12 indicative of the desired charge state of the defibrillator's storage capacitors. Those skilled in the art desiring further information concerning the construction and operation of the defibrillator 16 are referred to the Mirowski et al. U.S. Pat. No. 3,952,750.

The programmable microcontroller 12 also permits the bradycardia pacemaker to be operated in any one of several modes but, as will be explained in greater detail below, when being used to treat CHF, it is preferably programmed to operate in the AV sequential mode (VDD).

With continued reference to FIG. 1, and in accordance with the present invention, a circuit 58 is provided for sensing cardiac function which, as will be explained, may take on a number of specific forms. That is to say, there are a plurality of ways of assessing cardiac function, including systolic function and/or diastolic function of a heart, which may be incorporated into an implantable microcontroller based cardiac pacemaker. Thus, for example, the cardiac function sensing circuit may measure intracardiac impedance variations due to the influx and outflow of blood from one of the ventricular chambers. In this regard, reference is made to the Salo U.S. Pat. No. 4,686,987. Using this approach, it is possible to assess stroke volume, cardiac output, and peak dZ/dT.

The cardiac function sense circuit 56 may also comprise an accelerometer for measuring heart sounds. It is also contemplated that a micromachined or piezoelectric pressure transducer may be mounted on the lead 18 and positioned within the right ventricle, as at 58, where it is effective to measure right ventricular end-systolic or end-diastolic pressure, peak dP/dT or pulse pressure (systolic - diastolic). These parameters are well-known indicators of systolic function.

The cardiac function sense circuit 58 may also comprise a Doppler flow meter having a flow sensor operatively positioned relative to the aorta or pulmonary artery for measuring peak aortic or pulmonic flow or, alternatively, may be positioned for measuring tricuspid valve and mitral valve flow. Irrespective of the type of sensor, the information from the cardiac function sense circuit 58 is applied, via I/O module 44 and the system bus 36, to the microprocessor 34.

Before explaining the algorithm whereby the AV delay of the pacemaker can be adjusted to maximize cardiac function in a patient suffering from CHF, it is believed helpful to define certain parameters and, in this regard, reference is made to the several waveforms illustrated in FIG. 3:

Electromechanical interval (EMI)—This interval starts with atrial electrical activity (pace or sense) at point A and ends with the termination of the rapid filling phase, which is identified as the point labeled D.

Active Time (AT)—This interval starts with onset of ventricular electrical activity and ends with the completion of the filling phase of the heart, provided that the ventricles are refilled at their peak fast-filling rate.

Atrial cycle length (ACL)—the time between two successive atrial depolarization signals either paced or sensed.

Since EMI is the total time from the atrial electrical event to the end of fast filling, it is unnecessary to measure the individual components making up this interval, i.e., PEP, ET, MEFT, so long as there is a marker for the end of rapid filling. EMI is most readily measured as $AV_{int}+AT$, or as the time from atrial electric event, A, to the end of rapid filling, D, in the graph of FIG. 3.

Figure 4A:
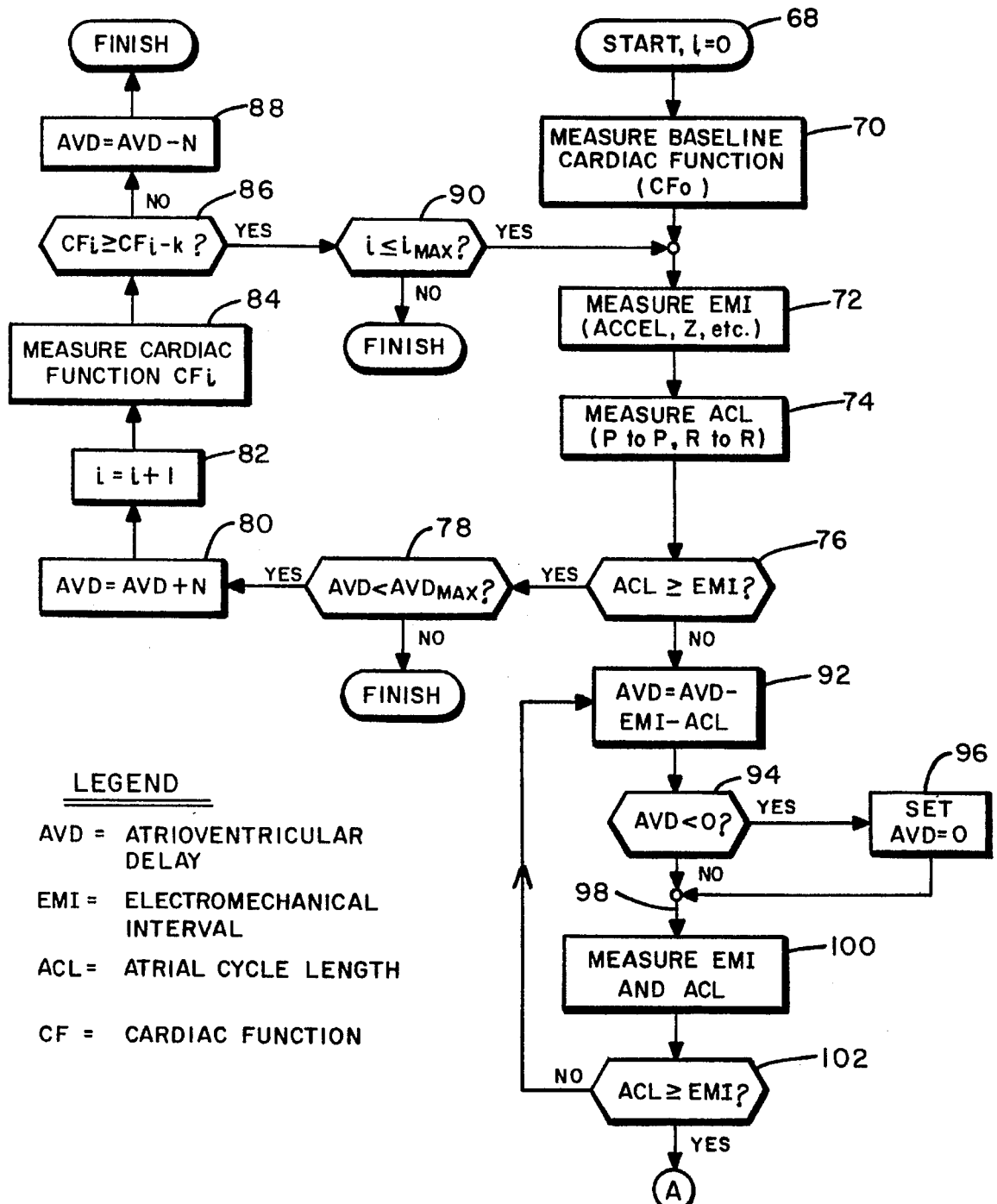
FIGS. 4A and 4B, when arranged as shown in FIG. 4, is a software flow diagram illustrating the algorithm executed by the microprogrammable controller in the pacemaker of FIG. 1.
Figure 4B:
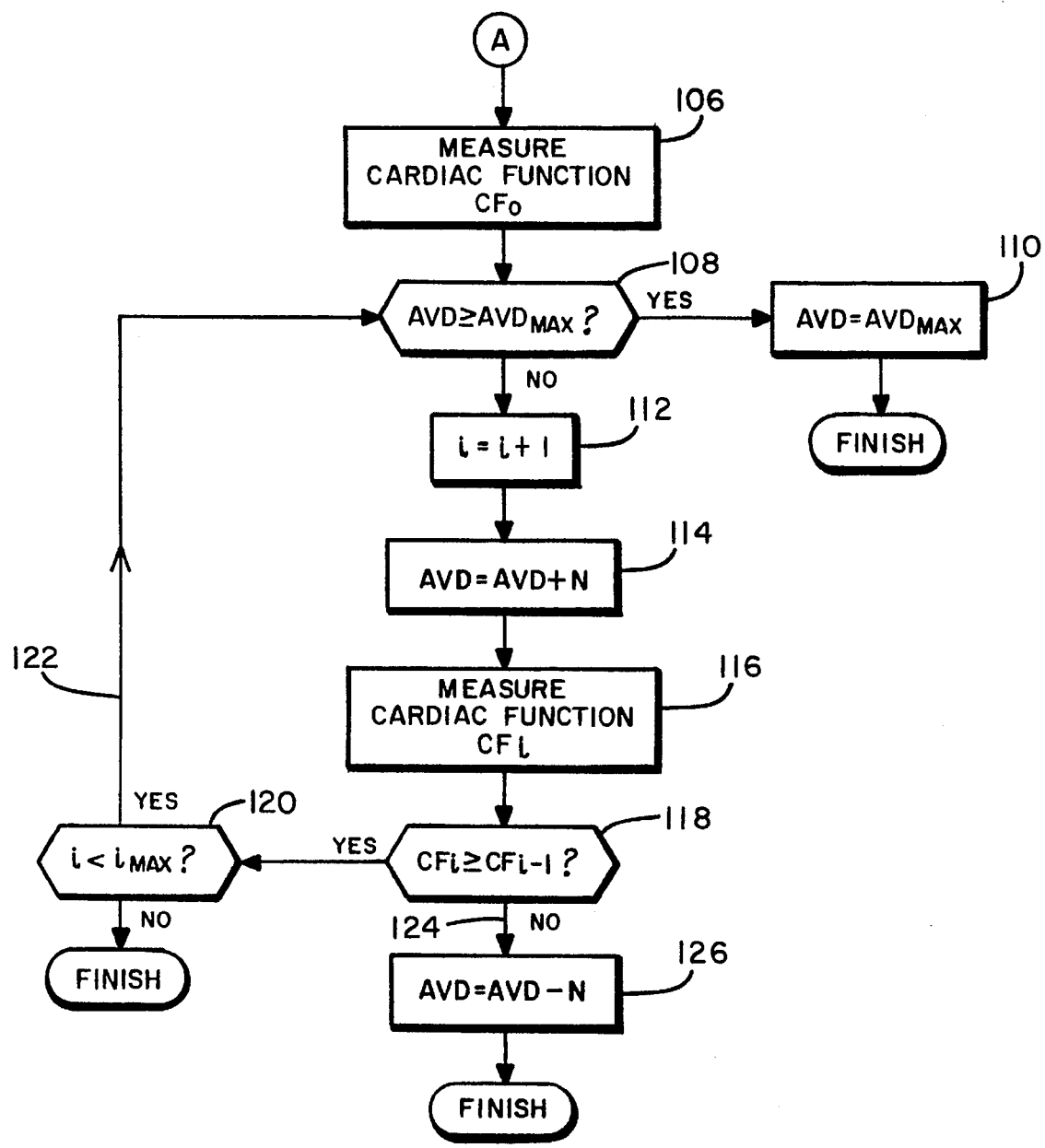

FIGS. 4A and 4B, when arranged as illustrated in FIG. 4, comprises a software flow diagram illustrating the algorithm executable by the microprocessor-based microprogrammable controller 12 used in adapting the dual-chamber, VDD pacemaker 14 of FIG. 1 to the treatment of CHF. In that the detailed coding of the software executable on the microprocessor comprising the implantable dual-chamber pacemaker constructed and operating in accordance with the present invention depends upon the specifics of the microprocessor employed and because the software flow diagrams presented herein are sufficient to permit those skilled in the art to program a microprocessor in such a way as to execute the algorithms depicted, it is deemed unnecessary to provide detailed coding in order to comply with the Patent Statutes.

With reference then to FIG. 4A, at the time the pacemaker is implanted, the software executes an initialization step wherein an index counter is set equal to zero (block 68). Next, the cardiac function sensor 58 provides an input to the microprogrammable controller 12 to provide a baseline cardiac function ($CF_0$) as represented by block 70. Next, the length of the electromechanical interval is measured using an accelerometer for measuring heart sounds and/or a means for measuring intracardiac impedance and/or any other sensor which gives information on the fast filling phase of the cardiac cycle. In that EMI is approximately equal to the sum of AV interval and Active Time, the technique disclosed in the co-pending Spinelli application, Ser. No. 07/806,626, filed Dec. 13, 1991, the content of which is hereby incorporated by reference, may be used for obtaining the Active Time measurement and, hence, the length of the EMI. The operation of measuring EMI is represented by block 72 in FIG. 4A. Following that operation, and as represented by block 74, the atrial cycle length is measured. This is either the P-to-P or the R-to-R interval and is readily determined by the pacemaker circuitry involved. Cardiac function, electromechanical interval and atrial cycle length measurements are preferably averaged over a predetermined number of heartbeats where the number to average over is a programmable parameter of the implanted pacemaker.

With initial or base-line values of cardiac function, EMI and ACL measured and stored, a test is made at block 76 to determine whether, with the initial AV delay value employed, the ACL is greater than or equal to EMI. If it is, a subsequent test is made, indicated by block 78, to determine whether the AV delay portion of EMI is less than a preprogrammed maximum value $AV_{max}$, such as 200 milliseconds. The value, $AV_{MAX}$, is also a programmable parameter. If the current AV delay value has not reached the predetermined maximum, a small time increment N is added to the AV delay interval (block 80). Typically, N may be 10 milliseconds, but again this quantity can be set to other values using an external programmer, via telemetry circuit 46. Following the incrementation of the AV delay value by the quantity, N, the cycle index is also incremented by one at block 82, and this is followed by a measurement of cardiac function with the incremented AV delay value in use. Once this measurement has been made (block 84), a test is made to determine whether the cardiac function just measured has increased over the measurement taken during a preceding cycle (block 86). If it has not, then the AV delay value is decremented by N milliseconds (block 88) and the implanted pacemaker continues to pace the patient's heart with the thus-established AV delay interval in place. Had the test at block 86 revealed that cardiac function had improved following the incrementing of the AV delay at block 80, then a further test is made at decision block 90 to determine whether the loop or index count, i, had reached a programmed maximum. If not, control returns to block 72 where again the EMI is measured with the new AV delay interval and control will continue to loop through steps 72–90 until the test at block 76 reveals that the atrial cycle length is less than the electromechanical interval.

The "NO" output from block 76 leads to block 92 and, as indicated by the legend therein, the AV delay of the pacemaker is adjusted by the difference between the electromechanical interval (EMI) and the atrial cycle length (ACL). This should guarantee that EMI will be approximately equal to ACL for successive measurements.

Following that operation, a test is made at block 94 to determine whether the newly computed AV delay value is negative and if it is, it is set equal to zero (block 96). Had AV delay been positive, control would have passed, via line 98, to the block 100 where EMI and ACL are again measured. Since ACL and EMI are functions of the AV delay, it is necessary to remeasure them after each change in the AV delay value.

Following the above measurement, the two are compared at block 102 to determine whether the ACL is equal to or greater than EMI. If not, control exits, via path 104, and loops back to operation block 92 and the same series of operations represented by blocks 92, 94, 96, 100 and 102 are repeated until the atrial cycle length exceeds or equals the electromagnetic interval.

Referring to FIG. 4B, once the test represented by block 102 is affirmed, the cardiac function sensor 58 operates to again measure the cardiac function associated with the current AV delay value (block 106). Having completed this measurement, a test is made at decision block 108 to determine whether the existing AV delay value for the pacemaker has reached or exceeded a preprogrammed maximum AV delay value. If it has, the AV delay value is set equal to the maximum AV delay value (block 110) and the pacemaker continues to pace the patient's heart with the maximum AV delay value being utilized. Had the test at decision block 108 revealed that the AV delay value employed had not reached the preprogrammed maximum value, the index or loop count, i, is incremented (block 112) and the current AV delay value is incremented by the programmed quantity N, as represented by operation block 114 in FIG. 4B. Once the AV delay value has been incremented by that quantity, the associated cardiac function is measured (block 116) and a test is made at block 118 to determine whether the newly measured cardiac function parameter exceeds the same parameter measured on an earlier cycle, thus establishing an improvement. If improvement is noted, a test is made to determine whether the index, i, has exceeded a programmed maximum value (block 120) and, if not, control passes via line 122 to the input of decision block 108 and control continues to loop through this path so long as there is an improvement in cardiac function noted on each iteration. At some point, a test made at block 118 will reveal that the cardiac function on a current cycle has worsened as compared to that on a immediately preceding cycle and, in that event, control exits block 118, via path 124, and, as indicated by block 126, the AV delay value then in use is decreased by the quantity, N, which, of course, corresponds to the previous cardiac function level.

It can be seen from the foregoing description of the flow diagram that the present invention provides an implantable cardiac rhythm management device having the ability to automatically adjust the AV delay value of the pacemaker to be the longest value consistent with maximum cardiac function for the particular patient in which the unit is implanted. This invention permits automatic adjustment without the need for making invasive tests to establish an AV delay quantity that is then set into a pacemaker using an external programmer. Being a closed loop arrangement, the pacemaker adapts itself to the particular patient as his systolic or diastolic function varies from optimum and without the need for physician intervention to readjust the AV delay parameter of the implanted pacemaker.

The cardiac rhythm management device further includes circuitry for converting ventricular tachycardia and/or ventricular fibrillation to sinus rhythm. A cardiac stimulator for treating congestive heart failure should include cardioverting circuitry in that, very commonly, patients suffering from CHF experience these lethal arrhythmias, even though the optimization of the AV interval in accordance with this invention improves the overall cardiac function for those patients.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method of operating an implantable cardiac stimulator implanted in a patient suffering from congestive heart failure, said cardiac stimulator being of the type having means for sensing atrial activity, means for sensing ventricular activity; means for sensing cardiac function of the patient's heart, means for stimulating only at least one ventricular chamber at a programmed rate, and microprogrammable controller means coupled to said means for sensing said atrial activity, said means for sensing ventricular activity, and said means for sensing cardiac function, said microprogrammable controller means controlling said means for stimulating only at least one ventricular chamber so as to issue ventricular stimulating pulses at said programmed rate at computed AV delay intervals following the sensing of an atrial event, comprising the steps of:

(a) adjusting said AV interval in incremental steps to a predetermined AV delay limiting value;

(b) for each of said incremental steps, monitoring a predetermined cardiac function of the heart to determine whether a given incremental change in said AV interval results in improved cardiac function; and (c) setting said AV interval at the greatest length less than or equal to the predetermined limiting value that yields maximal cardiac function.

2. A totally implantable cardiac stimulating apparatus for treating congestive heart failure comprising, in combination:

(a) means for sensing atrial activity;

(b) means for sensing ventricular activity;

(c) means for sensing cardiac output;

(d) ventricular stimulating means;

(e) a programmable microcontroller coupled to said atrial sensing means, said ventricular sensing means and said means for sensing cardiac output for producing control signals for controlling said ventricular stimulating means with said ventricular stimulating means generating ventricular stimulating pulses following AV delay intervals calculated by said programmable microcontroller from the sensing of atrial activity, said AV delay intervals being the shortest length yielding maximal cardiac function as derived from said cardiac output sensing means.

3. An implantable cardiac rhythm management device for treating CHF comprising, in combination:

(a) means for sensing intrinsic atrial activity;

(b) means for sensing intrinsic ventricular activity;

(c) means for sensing cardiac function;

(d) means responsive to said means for sensing intrinsic atrial activity and said means for sensing intrinsic ventricular activity for producing low energy cardiac stimulating pulses following an atrioventricular delay interval;

(e) means for applying said cardiac stimulating pulses solely to ventricular tissue; and (f) means responsive to said means for sensing cardiac function for modifying only the length of said atrioventricular delay interval in incremental steps so long as the modifications result in improvements in cardiac function.

4. The implantable cardiac rhythm management device as in claim 3 and further including:

(a) arrhythmia detecting means responsive to said means for sensing intrinsic ventricular activity;

(b) cardioverting means for producing high energy cardiac stimulating pulses; and (c) means for applying said high energy cardiac stimulating pulse to ventricular tissue when said arrhythmia detecting means senses potentially lethal arrhythmia.

5. The implantable cardiac rhythm management device as in claim 3 wherein said means for applying said cardiac stimulating pulses to ventricular tissue comprises:

(a) an elongated, flexible, pacing lead means coupled to said means for producing said low energy cardiac stimulating pulses and having stimulating electrodes thereon for contacting both ventricles of the heart.

* * * * *